(12) United States Patent
Marka et al.

(10) Patent No.: US 8,430,815 B2
(45) Date of Patent: Apr. 30, 2013

(54) COLOR TEMPERATURE CORRECTION

(75) Inventors: Rudolf Marka, Ismaning (DE); Dirk Fritze, Emmering (DE)

(73) Assignee: Trumpf Medizin Systems GmbH + Co. KG, Saalfeld (DE)

( * ) Notice: Subject to any disclaimer, the term of this patent is extended or adjusted under 35 U.S.C. 154(b) by 751 days.

(21) Appl. No.: 12/565,190

(22) Filed: Sep. 23, 2009

(65) Prior Publication Data

US 2010/0081887 A1 Apr. 1, 2010

(30) Foreign Application Priority Data

Sep. 30, 2008 (EP) .................................... 08017201

(51) Int. Cl.
  *A61B 1/06* (2006.01)
(52) U.S. Cl.
  USPC ........................................................ 600/249
(58) Field of Classification Search ................... 600/249
  See application file for complete search history.

(56) References Cited

U.S. PATENT DOCUMENTS

| 6,160,582 | A | 12/2000 | Hill |
| 6,597,396 | B1 | 7/2003 | Quendt et al. |
| 2005/0231945 | A1* | 10/2005 | Leibinger et al. ............. 362/231 |
| 2006/0291204 | A1 | 12/2006 | Marka et al. |
| 2008/0285820 | A1* | 11/2008 | Voelker ......................... 382/128 |

FOREIGN PATENT DOCUMENTS

| DE | 197 12 434 | 10/1998 |
| DE | 20 2007 007 054 | 8/2007 |
| EP | 0 933 973 | 11/1998 |
| EP | 1 568 938 | 8/2004 |
| EP | 1 722 157 | 5/2005 |
| JP | 2005-198750 | 7/2005 |

OTHER PUBLICATIONS

European Search Report from corresponding European Application No. EP 08 017 201.8, mailed Dec. 4, 2008, with English translation, 7 pages.

* cited by examiner

*Primary Examiner* — Nicholas Woodall
(74) *Attorney, Agent, or Firm* — Fish & Richardson P.C.

(57) ABSTRACT

A surgical lighting system includes a control device operable to adjust a color temperature of the surgical lamp, a camera, an image processing device, and means for transmitting color temperature information, corresponding to a set color temperature of the surgical lamp, to the image processing device.

22 Claims, 1 Drawing Sheet

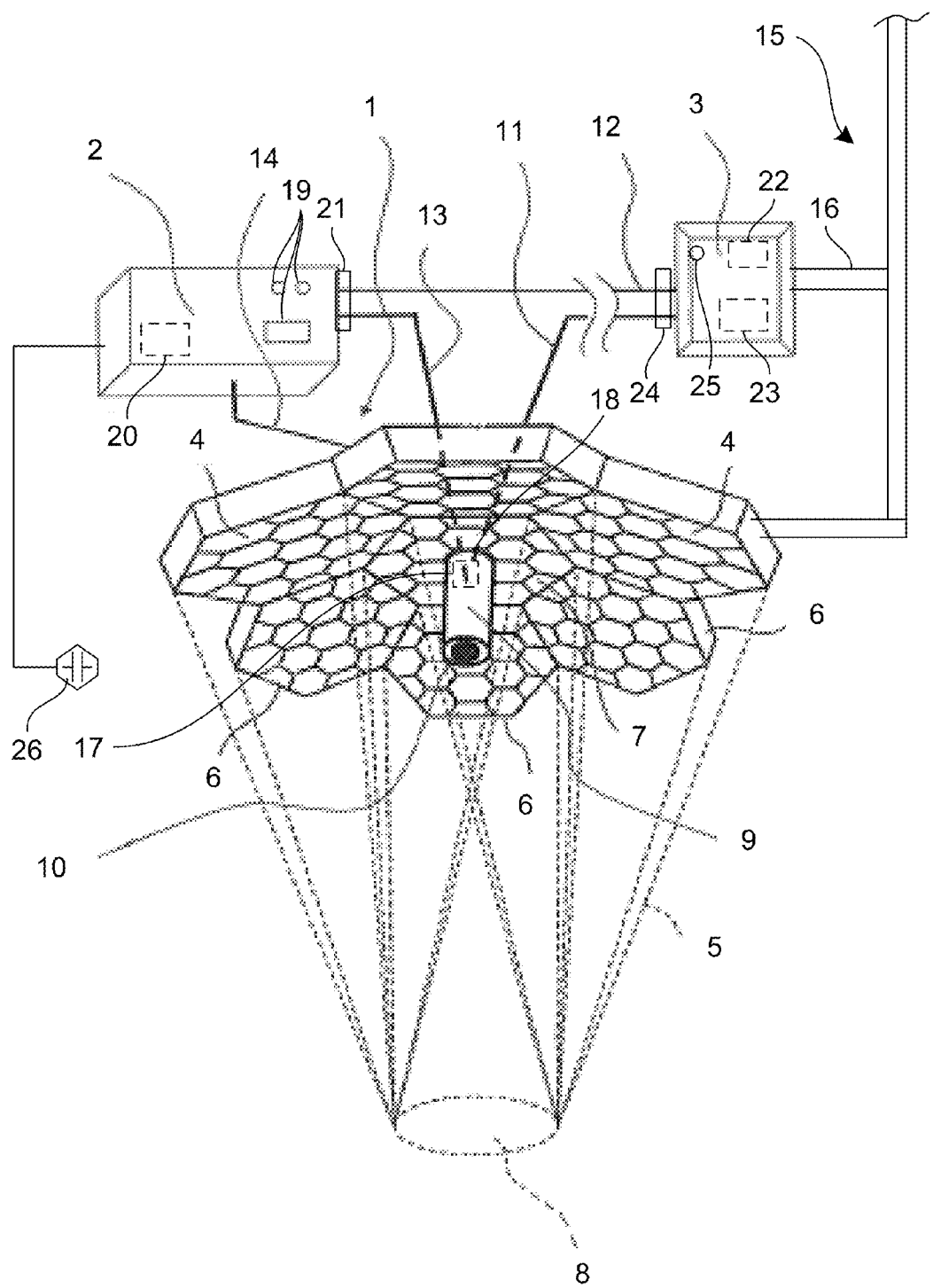

COLOR TEMPERATURE CORRECTION

RELATED APPLICATION

This application claims priority under 35 U.S.C. §119(a) to European Patent Application No. 08017201.8, filed on Sep. 30, 2008, the entire contents of which are hereby incorporated by reference.

TECHNICAL FIELD

This disclosure relates to color temperature correction of image signals in a surgical lighting system.

BACKGROUND

The use of LED technology in surgical lamps is known. In such surgical lamps, the color temperature of light emitted from the lamp can be adjusted in a determined range for a better discriminability of different types of tissue. As a result, it is possible to distinguish different kinds of tissue.

A surgical lamp employing LED technology is known from EP-A-1722157, which describes an arrangement in which the color temperature of the emitted light is created by various weighting of light sources emitting different spectra. A variation of the color temperature is possible in a range between 3,500 K and 5,000 K. The information about the emitted color temperature exists in the control of the surgical lamp. When changing the color temperature, the light intensity of the lamp is kept almost constant. The illuminants of the surgical lamp and their control units are calibrated in such a manner that the target settings of the control concerning the color temperature are exactly transformed to the real values.

Electronic cameras are also known. In one known example of an electronic camera, the incident light is transformed to voltage signals by sensors (CCD or CMOS). For capturing colored images, the light is color specifically captured by different sensors, which results in a color specific voltage signal, respectively. When displaying an image of an electronically captured video sequence, it can be beneficial to conduct white balance to reproduce the displayed image or the displayed video sequence in realistic colors.

A surgical lighting system is known from DE-A-20 2007 007 054 in which a communication between a lamp body and a camera takes place by calibration values that are transmitted from the lamp body to the camera by means of a bus system. The calibration values are experimentally determined. By means of this data transfer, the camera can appropriately adjust its white balance parameters, wherein a color-true rendering of the depicted operating area is guaranteed. The image signals are transmitted to a control device of the camera, and at the signal output of the control device, the image signals can be taken off for image processing apparatuses or for a monitor. By adjusting the color temperature at the lamp body, an adjustment of the camera takes place during the transmission of the image signals to the image processing apparatus or to the monitor so that an image having a color true rendering emerges.

SUMMARY

In general, this invention relates to color temperature correction of image signals in a surgical lighting system.

One aspect of the invention provides a surgical lighting system that includes a control device operable to adjust a color temperature of a surgical lamp, and a camera. The surgical lighting system also includes an image processing device, and means for transmitting color temperature information, corresponding to a set color temperature of the surgical lamp, to the image processing device.

Another aspect of the invention features a surgical lighting system that includes a control device operable to adjust a color temperature of a surgical lamp, an image processing device, and a camera configured to transmit image signals to the image processing device. The image processing device is configured to perform white balance adjustment on the image signals based, at least in part, on a set color temperature of the surgical lamp.

In another aspect, a surgical lighting system includes a control device operable to adjust a color temperature of a surgical lamp, a camera, and an image processing device. The control device is configured to transmit color temperature information, corresponding to a set color temperature of the surgical lamp, to the image processing device.

In yet another aspect, a method includes transmitting color temperature information, corresponding to a set color temperature of a surgical lamp, to an image processing device; transmitting an image signal from a camera to the image processing device; and performing white balance adjustment on the image signal with the image processing device based, at least in part, on the color temperature information.

Embodiments of the disclosed systems and methods may include one or more of the following features.

In some embodiments, the means for transmitting color temperature information includes a signal transmission link that connects the image processing device to the control device. The signal transmission link can include, for example, a signal cable, an infrared link, or a radio communication link.

In some cases, the image processing device is connected to a signal output of the camera.

In some embodiments, the surgical lighting system includes a sensor for detecting the set color temperature of the surgical lamp.

The surgical lighting system can also include a boom, and the image processing device can be supported by the boom.

In some cases, the control device is configured to transmit color temperature information to the image processing device periodically via the means for transmitting color temperature information.

In some embodiments, the control device is configured to transmit color temperature information to the image processing device, via the means for transmitting color temperature information, at least when the color temperature of the surgical lamp is changed.

The image processing device can be configured to automatically switch from a standby mode to an operating mode, in which the image processing device receives color temperature information from the control device, when the camera is recognized by the control device.

The control device can be configured to set a brightness of the surgical lamp, and the control device can be configured to transmit brightness information, corresponding to the brightness of light emitted from the surgical lamp, to the image processing device.

In some cases, the camera is connected to the control device.

In some embodiments, the control device, the camera, and the image processing device are connected via a data bus.

In some embodiments, the image processing device includes a memory storage. The memory storage includes stored color temperature correction values for multiple, different color temperature settings of the surgical lamp. The image processing device can be configured to perform white balance adjustment on the image signals based on the color temperature correction values.

In some cases, the surgical lighting system includes a signal transmission link (e.g., a signal cable, an infrared link, or a radio communication link) that connects the image processing device to the control device. The control device can be configured to transmit color temperature information to the image processing device via the signal transmission link.

In some embodiments, the surgical lighting system also includes a surgical lamp.

The control device can be configured to transmit color temperature information to the image processing device periodically. Alternatively or additionally, the control device can be configured to transmit color temperature information to the image processing device at least when the color temperature of the surgical lamp is changed.

Methods can also include providing the image processing device with color temperature correction parameters associated with multiple, different color temperature settings. The white balance adjustment is based, at least in part, on the color temperature correction parameters.

In some embodiments, methods can also include detecting the color temperature of the surgical lamp.

Other aspects, features, and advantages are in the description, drawings, and claims.

DESCRIPTION OF DRAWINGS

FIG. 1 is a schematic view of a surgical lighting system.

DETAILED DESCRIPTION

A surgical lamp 1 is attached to a ceiling, a wall or a movable stand by a carrying system 15 so that the surgical lamp 1 may be oriented within a range of activity in order to optimally illuminate an operating site during a surgical intervention. An image processing device (e.g., a monitor 3) is fixed to a boom 16 of the carrying system 15. However, the monitor 3 can also be attached to a medical supply unit, a stand or a device trolley.

The surgical lamp 1 includes illuminants 4 formed by LEDs having a refractor, which illuminate a light field 8 on the operating site by creating light beams 5. Each illuminant 4 is designed to illuminate the entire light field 8. Different-colored illuminants 4 (warm white, cold white, cyan, blue) are used in a specific number to create the spectrum of the natural daylight. By shifting performance data of the several illuminants 4, the color temperature of the emitted light can be varied between 3,500 K and 5,000 K.

The illuminants 4 are arranged in six outer modules 6 and one inner module 7. The bottom of the modules 6, 7 which forms the light emitting face, except for a small edge region, is filled with illuminants 4 on the entire light emitting face. The outer modules 6 are pivotably attached to the inner module 7 in order to focus the light beams 5 to the light field 8 on the operating site in different distances between the surgical lamp 1 and the operating site.

A handle 9 is provided in the center of the inner module 7. The handle 9 allows for sterile positioning of the surgical lamp 1. The handle 9 is formed by a sleeve made of sterilizable plastic, which is twistable fixed to a handle socket by means of an engagement button. By twisting the handle 9 about an angle of approximately 20° in the different directions of rotation, a switch is actuated, respectively, and by means of a drive motor, the outer modules 6 are either upwardly or downwardly pivoted to focus the outer modules 6 onto the light field 8. At the bottom, the sleeve of the handle 9 is provided with a clear glass plate, which allows the operating site to be viewed by a camera 10 (e.g., a CCD-camera) located inside the sleeve of the handle 9.

The camera 10 is fixed to a housing of the surgical lamp via a bayonet lock. By fixing the camera 10 to the housing of the surgical lamp 1, a plug connection 17 of a supply and signal line 13 and a video line 11 is automatically connected.

A captured image is transformed to electrical signals by CCD-sensors of the camera 10, which are accordingly amplified and transmitted from a signal output 18 via the plug connection 17 and the video line 11 through the housing of the surgical lamp 1 and the carrying system 15 to the monitor 3.

Inside the camera 10, motors are provided enabling the functions "zoom", "focus" and "image reorientation". The "zoom" function enables choosing the image section in a certain range of magnification or reduction. The "focus" function enables focusing the captured image. The "image reorientation" function enables the orientation of the image on the monitor 3 such that the image has the standard orientation (e.g. the viewing direction of the surgeon) after twisting the surgical lamp 1.

The control device 2 has the task to control the illumination functions of the surgical lamp 1 and the functions of the camera 10. Therefore, the control device 2 is connected to the camera 10 via the supply and signal line 13 and it is connected to the surgical lamp via a control line 14.

At the control device 2, there are operating elements 19 for switching the surgical lamp 1 on and off, for dimming (i.e., setting the brightness), for adjusting the color temperature, for setting the zoom factor of the camera 10, and for driving the motor for "image reorientation". Within the control device 2, an electronic control 20 is provided. The operating elements 19 are connected to the electronic control 20 and they send signals to the electronic control 20, which generates the appropriate commands for the actuators which are the motors of the camera 10 and the power control elements of the illuminants 4 of the surgical lamp 1.

The control device 2 is depicted as a separate assembly. However, the control device 2 can be integrated in the surgical lamp 1 in order to shorten the lengths of the lines.

The control device 2 is connected to the monitor 3 via a signal transmission link (e.g., a signal cable 12), and it transfers the signals to the monitor 3 via an interface 21 (e.g., RS 232).

The monitor 3 includes a storage area 22 (e.g., memory) for storing the parameter data sets (Setup) for the color temperature correction, which is the white balance of the displayed image besides the conventional display device (e.g., an LCD-display), and a controller 23 for processing image signals (e.g., video signals) transmitted from the camera 10 to a visible image on the LCD-display.

The parameters for the color temperature correction of the separate color temperatures adjustable at the surgical lamp 1 are empirically determined and stored in the storage area. The parameters characterize the deviation of the color point of the transmitted image signal from the actual color point of a captured pixel.

The monitor 3 includes an interface 24 (e.g., RS 232) in order to transform a color temperature signal transmitted from the control device 2, into a data set that is identifiable by the controller 23 of the monitor 3.

The surgical lamp 1, the control device 2, the camera 10 and the monitor 3 can be connected by a RS 232-bus. Alternatively or additionally, these system components can be connected by separate data lines.

In use, the camera 10 transmits image signals which are formed by the brightness (Y) and the color point (UV-coordinates) of a YUV-signal of a pixel via the video line 11 to the monitor 3. The received image signals of the color point are modified according to the stored correction values for the set color temperature, which are chosen based on the data concerning the set color temperature transmitted via the signal cable 12.

The set color temperature is transmitted only in case of an alteration to the monitor 3. Therefore, the amount of data transmitted via the bus is reduced. Alternatively, the transmission can be periodically performed, which enhances the safety against failures.

The signal transmission between the control device 2 and the monitor 3 can be made via the signal cable 12. Alternatively or additionally, signal transmission between the control device 2 and the monitor 3 can be done via another kind of data transmission, e.g. an infrared interface or radio communication.

The brightness of the monitor 3 can be set by a brightness regulator 25. A further possibility for setting the brightness is coupling the brightness of the monitor 3 and the set brightness of the surgical lamp 1. For example, the control device 2 can be configured to send a brightness signal, corresponding to the set brightness of the surgical lamp 1, to the monitor 3. The monitor 3 can then adjust the brightness of the displayed image based on the brightness signal. The brighter the surgical lamp shines, the brighter the image of the monitor 3 is set. This coupling can be switched off in order to avoid unwanted variations of the brightness of the monitor 3.

A further possibility is merely distinguishing a set of an endo-mode of the surgical lamp 1. In the endo-mode, the surgical lamp 1 is operated at about 10% of its maximum luminosity in order to enable a better recognizability of the image displayed at the monitor 3 for the surgeon. At this setting of the control, a corresponding signal is sent from the control device 2 via the signal cable 12 to the monitor 3 and the monitor is operated with a reduced brightness in order to avoid blinding the surgeon. At the return from the endo-mode to a higher luminosity, the corresponding signal is sent from the control device 2 to the monitor 3 and the image of the monitor 3 is set brighter again.

A further function is the automatic switching-on of the monitor 3 when the camera 10 is connected. As soon as the camera is connected, e.g., by the plug connection, the camera 10 sends a corresponding signal via the supply and signal line 13 to the control device 2. As a result, the control device 2 recognizes that the camera 10 is connected to the surgical lamp 1 and it sends a corresponding signal via the signal cable 12 to the monitor 3. Then, an automatic activation of the monitor 3 occurs from a standby mode as well as a changeover to an appropriate input having an applied signal.

Alternatively or additionally, a sensor 26 for detecting the color temperature of the emitted light can be provided. Sensor data, corresponding to the detected color temperature of the emitted light, can be transmitted to the control device 2. The sensor data can be processed by the control device 2 and sent via the signal cable 12 to the monitor 3, which corrects the color temperature based on the sensor data. Optionally, the color temperature sensor 26 can send an appropriately processed signal to the monitor 3, which then performs the color temperature correction based on the processed signal.

The camera 10 does not necessarily have to be fixed to the surgical lamp 1. For example, the camera 10 can be attached at the carrying system of the surgical lamp 1 or at a separate stand.

The use of an arbitrary camera 10 is possible because the white balance of the camera 10 can fixedly be set and the variation of the color temperature of the illuminated surgical field is directly sent from the surgical lamp 1 to the image processing device (e.g., monitor 3).

A number of embodiments of the invention have been described. Nevertheless, it will be understood that various modifications may be made without departing from the spirit and scope of the invention. Accordingly, other embodiments are within the scope of the following claims.

What is claimed is:

1. A surgical lighting system comprising:
   a control device operable to adjust a color temperature of a surgical lamp;
   a camera;
   an image processing device; that is separate from the camera and that comprises a memory storage including stored color temperature correction values for multiple, different color temperature settings of the surgical lamp; and
   means for transmitting color temperature information, corresponding to a set color temperature of the surgical lamp, to the image processing device.

2. The surgical lighting system of claim 1, wherein the means for transmitting color temperature information comprises a signal transmission link connecting the image processing device to the control device.

3. The surgical lighting system of claim 2, wherein the signal transmission link is selected from the group consisting of a signal cable, an infrared link, and a radio communication link.

4. The surgical lighting system of claim 1, wherein the image processing device is connected to a signal output of the camera.

5. The surgical lighting system of claim 1, further comprising a sensor for detecting the set color temperature of the surgical lamp.

6. The surgical lighting system of claim 1, further comprising a boom, wherein the image processing device is supported by the boom.

7. The surgical lighting system of claim 1, wherein the control device is configured to transmit color temperature information to the image processing device periodically via the means for transmitting color temperature information.

8. The surgical lighting system of claim 1, wherein the control device is configured to transmit color temperature information to the image processing device, via the means for transmitting color temperature information, at least when the color temperature of the surgical lamp is changed.

9. The surgical lighting system of claim 1, wherein the image processing device is configured to automatically switch from a standby mode to an operating mode, in which the image processing device receives color temperature information from the control device, when the camera is recognized by the control device.

10. The surgical lighting system of claim 1, wherein the control device is configured to set a brightness of light emitted from the surgical lamp, and wherein the control device is configured to transmit brightness information, corresponding to the set brightness of the surgical lamp, to the image processing device.

11. The surgical lighting system of claim 1, wherein the camera is connected to the control device.

12. The surgical lighting system of claim 1, wherein the control device the camera, and the image processing device are connected via a data bus.

13. The surgical lighting system of claim 1, wherein the image processing device is a monitor.

14. A surgical lighting system:
- a control device operable to adjust a color temperature of a surgical lamp;
- a camera; and
- an image processing device; that is separate from the camera and that comprises a memory storage including stored color temperature correction values for multiple, different color temperature settings of the surgical lamp,
- wherein the camera is configured to transmit image signals to the image processing device, and the image processing device is configured to perform white balance adjustment on the image signals based, at least in part, on a set color temperature of the surgical lamp.

15. The surgical lighting system of claim 14, wherein the image processing device is configured to perform white balance adjustment on the image signals based on the stored color temperature correction values.

16. The surgical lighting system of claim 14, further comprising a sensor for detecting the set color temperature of the surgical lamp.

17. The surgical lighting system of claim 14, comprising a signal transmission link connecting the image processing device to the control device, wherein the control device is configured to transmit color temperature information to the image processing device via the signal transmission link.

18. The surgical lighting system of claim 17, wherein the signal transmission link is selected from the group consisting of a signal cable, an infrared link, and a radio communication link.

19. A surgical lighting system comprising:
- a control device operable to adjust a color temperature of a surgical lamp;
- a camera; and
- an image processing device, that comprises a memory storage including stored color temperature correction values for multiple, different color temperature settings of the surgical lamp,
- wherein the control device is configured to transmit color temperature information, corresponding to a set color temperature of the surgical lamp, to the image processing device.

20. The surgical lighting system of claim 19, comprising a signal transmission link connecting the image processing device to the control device, wherein the control device is configured to transmit color temperature information to the image processing device via the signal transmission link.

21. The surgical lighting system of claim 20, wherein the signal transmission link is selected from the group consisting of a signal cable, an infrared link, and a radio communication link.

22. The surgical lighting system of claim 20, wherein the image processing device is a monitor.

* * * * *

UNITED STATES PATENT AND TRADEMARK OFFICE
CERTIFICATE OF CORRECTION

PATENT NO. : 8,430,815 B2  
APPLICATION NO. : 12/565190  
DATED : April 30, 2013  
INVENTOR(S) : Rudolf Marka and Dirk Fritze Page 1 of 1

It is certified that error appears in the above-identified patent and that said Letters Patent is hereby corrected as shown below:

On the Title page, item (73), under Assignee, delete "Systems" and insert --Systeme--.

Signed and Sealed this  
Sixteenth Day of July, 2013

Teresa Stanek Rea  
*Acting Director of the United States Patent and Trademark Office*